United States Patent
Narasimhan et al.

(10) Patent No.: US 9,636,029 B1
(45) Date of Patent: May 2, 2017

(54) ADAPTIVE SELECTION OF DIGITAL ECG FILTER

(71) Applicant: Vital Connect, Inc., Campbell, CA (US)

(72) Inventors: Ravi Narasimhan, Sunnyvale, CA (US); Nersi Nazari, Atherton, CA (US); Nima Ferdosi, San Jose, CA (US)

(73) Assignee: VITAL CONNECT, INC., San Jose, CA (US)

( * ) Notice: Subject to any disclaimer, the term of this patent is extended or adjusted under 35 U.S.C. 154(b) by 40 days.

(21) Appl. No.: 13/828,544

(22) Filed: Mar. 14, 2013

(51) Int. Cl.
*A61B 5/0402* (2006.01)
*A61B 5/04* (2006.01)
*A61B 5/0456* (2006.01)
*A61B 5/00* (2006.01)

(52) U.S. Cl.
CPC ........ *A61B 5/04017* (2013.01); *A61B 5/0456* (2013.01); *A61B 5/7203* (2013.01)

(58) Field of Classification Search
CPC ... A61B 5/0402; A61B 5/0245; A61B 5/7203; A61B 5/04017; A61B 5/0456; A61B 5/04012; A61B 5/7207
USPC ................................................. 600/508, 521
See application file for complete search history.

(56) References Cited

U.S. PATENT DOCUMENTS

| | | | | |
|---|---|---|---|---|
| 5,617,871 A * | 4/1997 | Burrows | ............ | A61B 5/0002 128/903 |
| 2002/0045920 A1* | 4/2002 | Thompson | ............ | A61N 1/025 607/60 |
| 2007/0239220 A1* | 10/2007 | Greenhut | ............ | A61B 5/0452 607/32 |
| 2009/0318820 A1* | 12/2009 | Toledo | ............ | A61B 5/04014 600/509 |
| 2010/0056884 A1* | 3/2010 | Kwok | ............ | A61B 5/053 600/301 |
| 2010/0114198 A1* | 5/2010 | Donofrio | ............ | A61N 1/36114 607/4 |
| 2012/0071730 A1* | 3/2012 | Romero | ............ | A61B 5/046 600/301 |
| 2012/0232417 A1* | 9/2012 | Zhang | ............ | A61N 1/3702 600/518 |
| 2013/0245478 A1* | 9/2013 | Zhang | ............ | A61B 5/0402 600/521 |

\* cited by examiner

*Primary Examiner* — Michael Kahelin
*Assistant Examiner* — Minh Duc Pham
(74) *Attorney, Agent, or Firm* — Brundidge & Stanger, P.C.

(57) ABSTRACT

A method and system for filtering a detected ECG signal are disclosed. In a first aspect, the method comprises filtering the detected ECG signal using a plurality of digital filters. The method includes adaptively selecting one of the plurality of digital filters to maintain a minimum signal-to-noise ratio (SNR). In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to carry out the steps of the method.

11 Claims, 12 Drawing Sheets

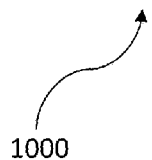

| Quality Metric | QRS amplitude | Activity Level | Diagnosis | Action |
|---|---|---|---|---|
| High | High | High | Normal ECG | None |
| High | High | Low | Normal ECG | None |
| High | Low | High | Weak but clean ECG | Use digital Gain |
| High | Low | Low | Weak but clean ECG | Use digital Gain |
| Low | High | High | Noisy ECG due to motion artifact, bad contact or wrong placement | Warn user or wait for the activity to become low and re-assess. |
| Low | High | Low | Noisy ECG due to bad contact or wrong placement | Warn user if it persists. |
| Low | Low | High | Noisy ECG due to bad contact or wrong placement | Warn user if it persists. |
| Low | Low | Low | Noisy ECG due to bad contact or wrong placement | Warn user if it persists. |

ADAPTIVE SELECTION OF DIGITAL ECG FILTER

FIELD OF THE INVENTION

The present invention relates to sensors, and more particularly, to a sensor device utilized to measure ECG signals using adaptive selection of digital filters.

BACKGROUND

A sensor device can be placed on the upper-body of a user (e.g. chest area) to sense an analog, single-lead, bipolar electrocardiogram (ECG) signal through electrodes that are attached to the skin of the user. The analog ECG signal is sampled and converted to the digital domain using an analog-to-digital converter (ADC) and is passed to a signal processing unit of the sensor device to extract R wave to R wave intervals (RR intervals) and other related features of the ECG signal.

Typically, several ambient noises such as motion artifacts and baseline wander, caused by the movement of the user, are mixed with the ECG signal and thus picked up by the sensor device resulting in less accurate ECG signal detection. Conventional methods of filtering detected ECG signals include filtering the ECG signal using a fixed analog anti-aliasing filter before the ECG signal is converted to the digital domain by an ADC and then filtering the ECG signal using a digital band-pass filter that removes the baseline wander and the out of the band noise.

However, these conventional methods do not adequately filter ECG signals with changing parameters. Therefore, there is a strong need for a cost-effective solution that overcomes the above issue. The present invention addresses such a need.

SUMMARY OF THE INVENTION

A method and system for filtering a detected ECG signal are disclosed. In a first aspect, the method comprises filtering the detected ECG signal using a plurality of digital filters. The method includes adaptively selecting one of the plurality of digital filters to maintain a minimum signal-to-noise ratio (SNR).

In a second aspect, the system comprises a wireless sensor device coupled to a user via at least one electrode, wherein the wireless sensor device includes a processor and a memory device coupled to the processor, wherein the memory device stores an application which, when executed by the processor, causes the processor to filter the detected ECG signal using a plurality of digital filters. The system further causes the processor to adaptively select one of the plurality of digital filters to maintain a minimum signal-to-noise ratio (SNR).

BRIEF DESCRIPTION OF THE DRAWINGS

The accompanying figures illustrate several embodiments of the invention and, together with the description, serve to explain the principles of the invention. One of ordinary skill in the art will recognize that the embodiments illustrated in the figures are merely exemplary, and are not intended to limit the scope of the present invention.

FIG. 10 illustrates a table of user notifications in accordance with an embodiment.

DETAILED DESCRIPTION

Figure 1:
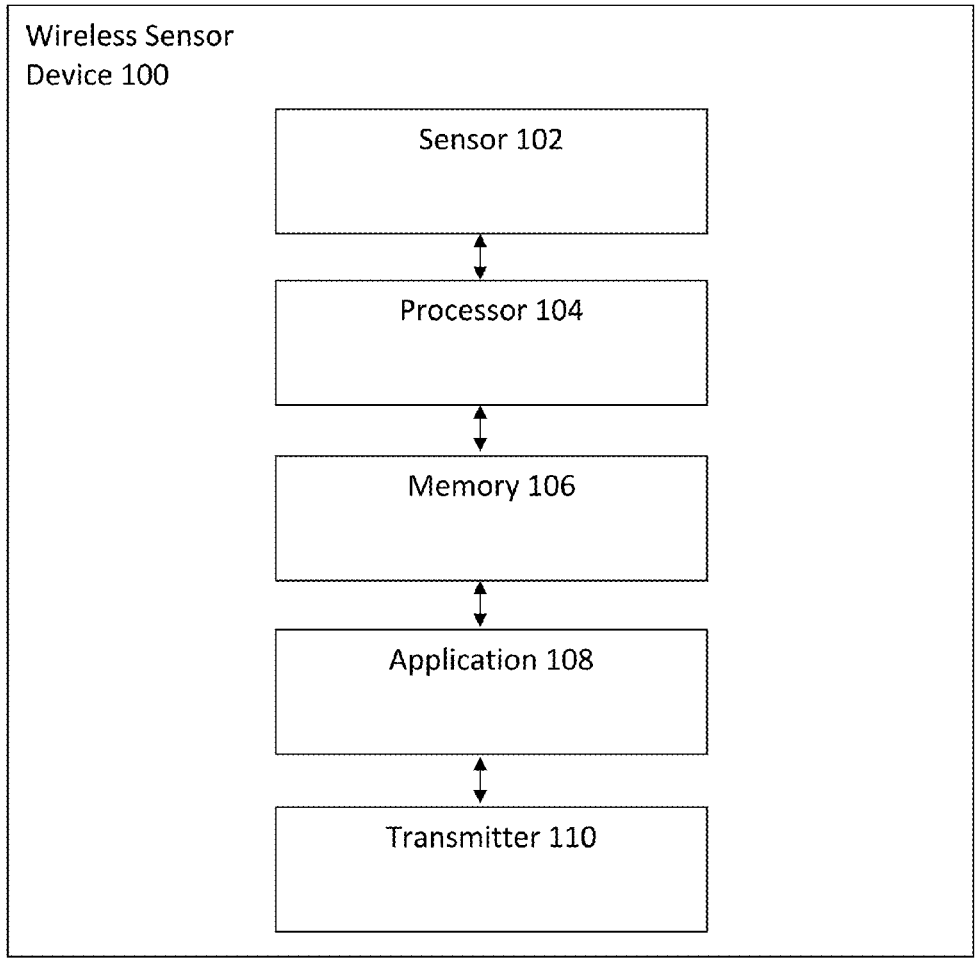
FIG. 1 illustrates a wireless sensor device in accordance with an embodiment.

The present invention relates to sensors, and more particularly, to a sensor device utilized to measure ECG signals using adaptive selection of digital filters. The following description is presented to enable one of ordinary skill in the art to make and use the invention and is provided in the context of a patent application and its requirements. Various modifications to the preferred embodiment and the generic principles and features described herein will be readily apparent to those skilled in the art. Thus, the present invention is not intended to be limited to the embodiments shown but is to be accorded the widest scope consistent with the principles and features described herein.

Utilizing a combination of adaptive filters, a sensor device more accurately detects the ECG signal of a user over conventional fixed filter methodologies. A method and system in accordance with the present invention filters a detected ECG signal using a predetermined number of parallel digital band-pass filters (e.g. 4) with varying 3 dB high-pass cutoff frequencies (e.g. 1, 5, 10, and 20 Hz). By adaptively changing the digital filter whose output is used for RR interval (or other related features) calculation, a minimum signal-to-noise ratio (SNR) for the ECG signal is maintained.

During sensing, the sensor device does not have a reference ECG signal available to conventionally measure noise and the SNR of the ECG signal. Thus, the sensor device utilizes a Quality Metric (QM) for each of the predetermined number of parallel digital band-pass filters to estimate the SNR of the ECG signal. Because calculation of a Quality Metric results in power consumption by a microprocessor of the sensor device, the Quality Metric at each digital filter output can be calculated one at a time. Additionally, the sensor device utilizes activity level data or a level of user motion registered on a MEMS device embedded within the sensor device to measure noise and ECG signal quality. The measured QM and activity level data are both utilized by the sensor device as criteria for adaptive selection and changing of the digital filter.

The method and system in accordance with the present invention ensures that frequent switching between different digital filters is eliminated. Frequent switching is undesirable because every time a filter is switched, there is a settling time and lag that affects the continuous and accurate measurement of the ECG signal. By determining whether a minimum ECG Quality Metric is maintained, the sensor device ensures that a digital filter is not changed even though the Quality Metric output of one or more of the other digital filters is higher. The resulting hysteresis ensures stability in the selection of the digital filter and prevents erratic switching between digital filters based on transient and short bursts of noise.

One of ordinary skill in the art readily recognizes that a variety of sensor devices can be utilized to measure ECG signals using adaptive selection of digital filters including portable wireless sensor devices with embedded circuitry in a patch form factor and that would be within the spirit and scope of the present invention.

To describe the features of the present invention in more detail, refer now to the following description in conjunction with the accompanying Figures.

FIG. 1 illustrates a wireless sensor device 100 in accordance with an embodiment. The wireless sensor device 100 includes a sensor 102, a processor 104 coupled to the sensor 102, a memory 106 coupled to the processor 104, an application 108 coupled to the memory 106, and a transmitter 110 coupled to the application 108. The sensor 102 obtains data from the user and transmits the data to the memory 106 and in turn to the application 108. The processor 104 executes the application 108 to process ECG signal information of the user. The information is transmitted to the transmitter 110 and in turn relayed to another user or device.

In one embodiment, the sensor 102 comprises two electrodes to measure cardiac activity and a MEMS device (e.g. accelerometer) to record physical activity levels and the processor 104 comprises a microprocessor. One of ordinary skill in the art readily recognizes that a variety of devices can be utilized for the processor 104, the memory 106, the application 108, and the transmitter 110 and that would be within the spirit and scope of the present invention.

Figure 2:
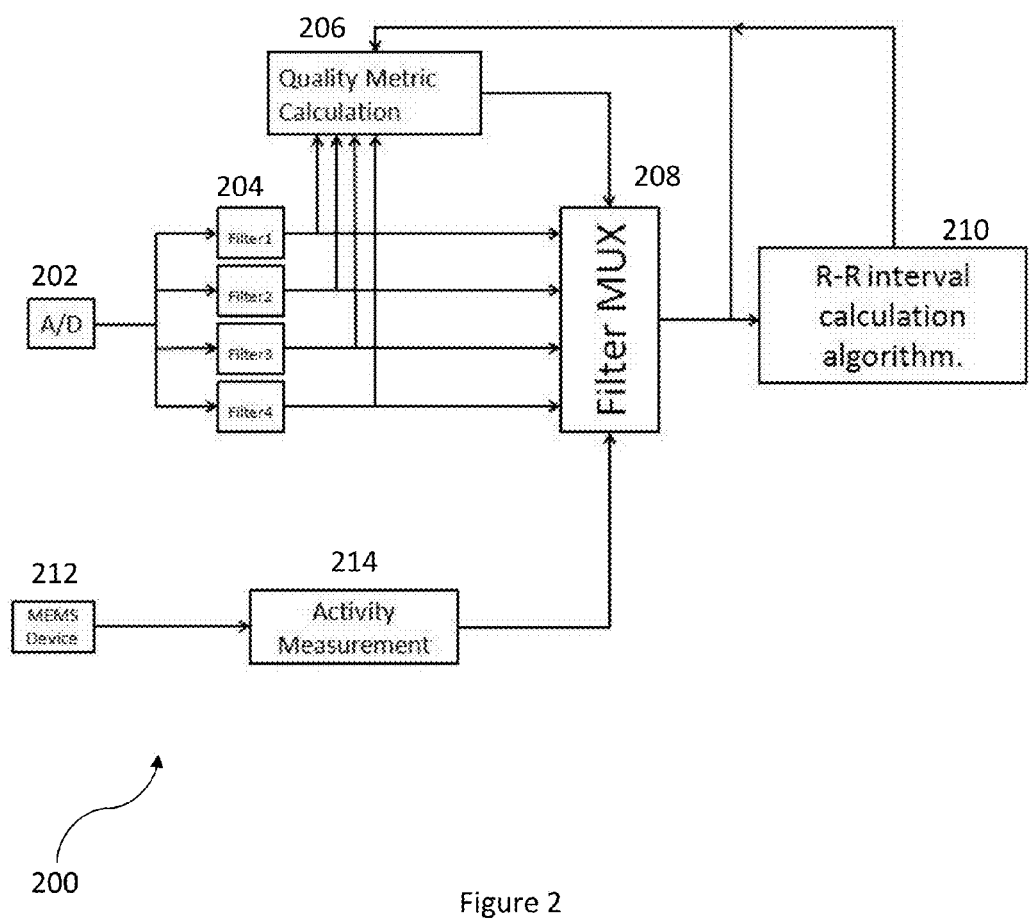
FIG. 2 illustrates a block diagram of adaptive filter selection in accordance with an embodiment.

FIG. 2 illustrates a block diagram 200 of adaptive filter selection in accordance with an embodiment. The block diagram 200 includes an analog-to-digital converter A/D 202, four digital filters 204 coupled to the A/D 202, a quality metric calculation unit 206 coupled to the four digital filters 204, to a filter multiplexer (MUX) 208, and to a R-R interval calculation algorithm unit 210. One of ordinary skill in the art readily recognizes that different number of digital filters can be coupled to the A/D including but not limited to 4, 6, and 10 filters and that would be within the spirit and scope of the present invention. The block diagram 200 also includes a MEMS device 212 coupled to an activity measurement unit 214, wherein the activity measurement unit 214 is coupled to the filter MUX 208.

In FIG. 2, ECG signals are detected by the sensor 102 of the wireless sensor device 100 and transmitted to the A/D 202. Additionally, in FIG. 2, physical movements of the user are detected by the MEMS device 212. After receiving the ECG signals and converting them to the digital domain, the A/D 202 transmits the signals through the four digital filters 204 and to the quality metric calculation unit 206 which calculates a Quality Metric for each filter individually to preserve processing power.

The filter MUX 208 receives each of these calculated Quality Metric values which aids in the selection of which digital filter to use for the R-R interval calculation by the R-R interval calculation algorithm unit 210. After detecting the physical movements of the user, the MEMS device 204 transmits the data to the activity measurement unit 214 to calculate activity levels and to transmit the calculated activity levels to the filter MUX 208 which also aids in the selection of which digital filter to use for the R-R interval calculation by the R-R interval calculation algorithm unit 210.

In one embodiment, calculation of the Quality Metric includes both a statistical quality indicator component and a mid-beat signal-to-noise ratio (SNR) quality indicator component. As a result of a lack of a reference ECG signal available during the time of sensing, statistical properties and parameters of the motion artifacts, background noise, and the ECG signal are utilized to assess the quality of the ECG signal. For statistical parameters to accurately capture the quality of the ECG signal, a large number of data samples is required. Therefore, the statistical parameters are typically not sensitive to faster changes in signal quality.

Using only statistical parameters as a signal quality indicator has the drawback of having a low sensitivity to small noise power level. Therefore, the statistical quality indicator component is combined with the mid-beat SNR quality indicator component. The mid-beat SNR quality indicator component utilizes already detected QRS peaks of the ECG signal to estimate the signal-to-noise ratio. Combining both the statistical and mid-beat SNR quality indicator components results in a Quality Metric calculation that provides high sensitivity for different levels of noise.

An ECG signal has a sharp peak in the probability density function in contrast to background noise which has a flatter distribution. The noisier the ECG signal, the flatter the distribution of the combination of ECG signal and noise. In one embodiment, a Kurtosis algorithm is utilized to measure sharp peaks of the distribution of a random variable. Kurtosis of a random variable (x) is defined as $Kurtosis(x)=(E(x-m)^4)/(E((x-m)^2)^2)$, where $E(x)$ is the expected value of the random variable x and $m=E(x)$. Kurtosis of the ECG signal is a good indicator of the level of noise corrupting the ECG signal. Therefore, calculation of the Kurtosis of the ECG signal represents the statistical quality indicator component of the Quality Metric.

One of ordinary skill in the art readily recognizes that an ECG signal has a high Kurtosis including but not limited to a value greater than approximately 10, a pure Gaussian signal has a Kurtosis including but not limited to a value of approximately 3, and a motion artifact noise corrupting the ECG signal has a Kurtosis including but not limited to a value of approximately between 2 and 5, and that would be within the spirit and scope of the present invention.

Figure 3:
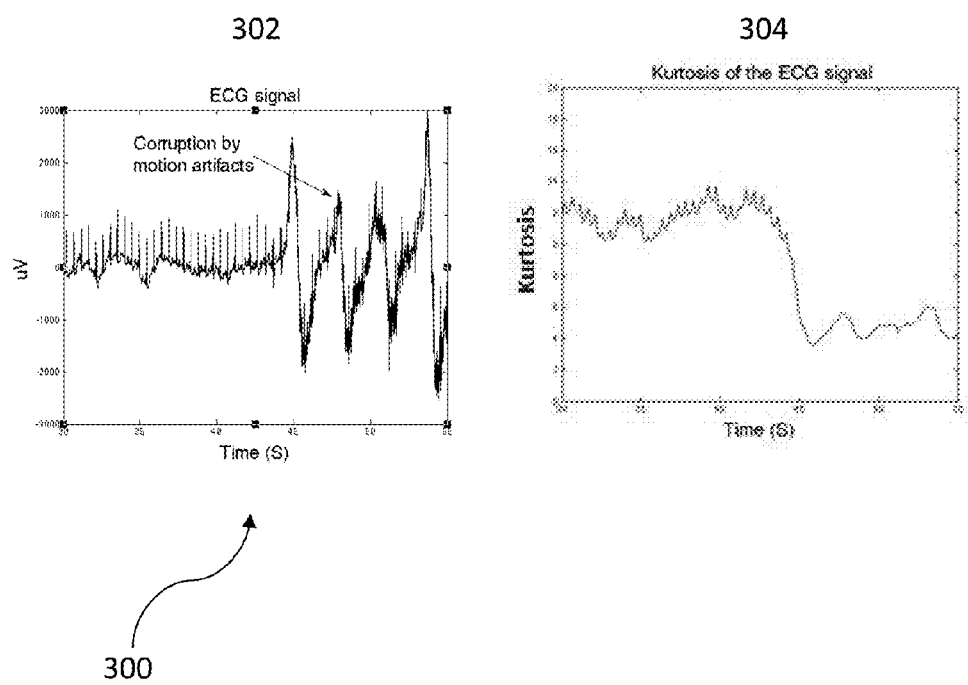
FIG. 3 illustrates a diagram of Kurtosis of an ECG signal in accordance with an embodiment.

FIG. 3 illustrates a diagram 300 of Kurtosis of an ECG signal in accordance with an embodiment. In the diagram 300, the left FIG. 302 shows an ECG signal corrupted by motion artifacts and the right FIG. 304 shows Kurtosis of an ECG signal that decreases when combined with motion artifact and noise corruption.

Successive QRS peaks of the ECG signal are analyzed for the calculation of the mid-beat signal-to-noise ratio (SNR) quality indicator component. Part of the ECG signal is called the TP segment. The TP segment denotes the area of the ECG signal that is between the end of a T wave of the previous beat and the start of a P wave of the next beat. Under optimal conditions (e.g. very little to no noise corrupting the ECG signal), the TP segment is at a flat baseline. By computing the variance of the ECG signal over a predetermined time period window in the middle of the TP segment, an estimate of the noise power or amount of noise corrupting the ECG signal is garnered.

To compute the mid-beat signal-to-noise ratio (SNR) quality indicator component, a ratio of Signal Power over Noise Power (mid-beat SNR=Signal Power/Noise Power) is calculated. Noise Power is calculated as a variance of the ECG signal over a predetermined time period window in the middle of the TP segment is averaged over a plurality of beats. Signal Power is calculated as an average of the RS amplitude squared over the plurality of beats. In one embodiment, a mid-point between two detected R peaks of successive heartbeats is utilized for the mid-beat SNR quality indicator component calculation instead of detecting the T and P waves to lower power consumption.

Figure 4:
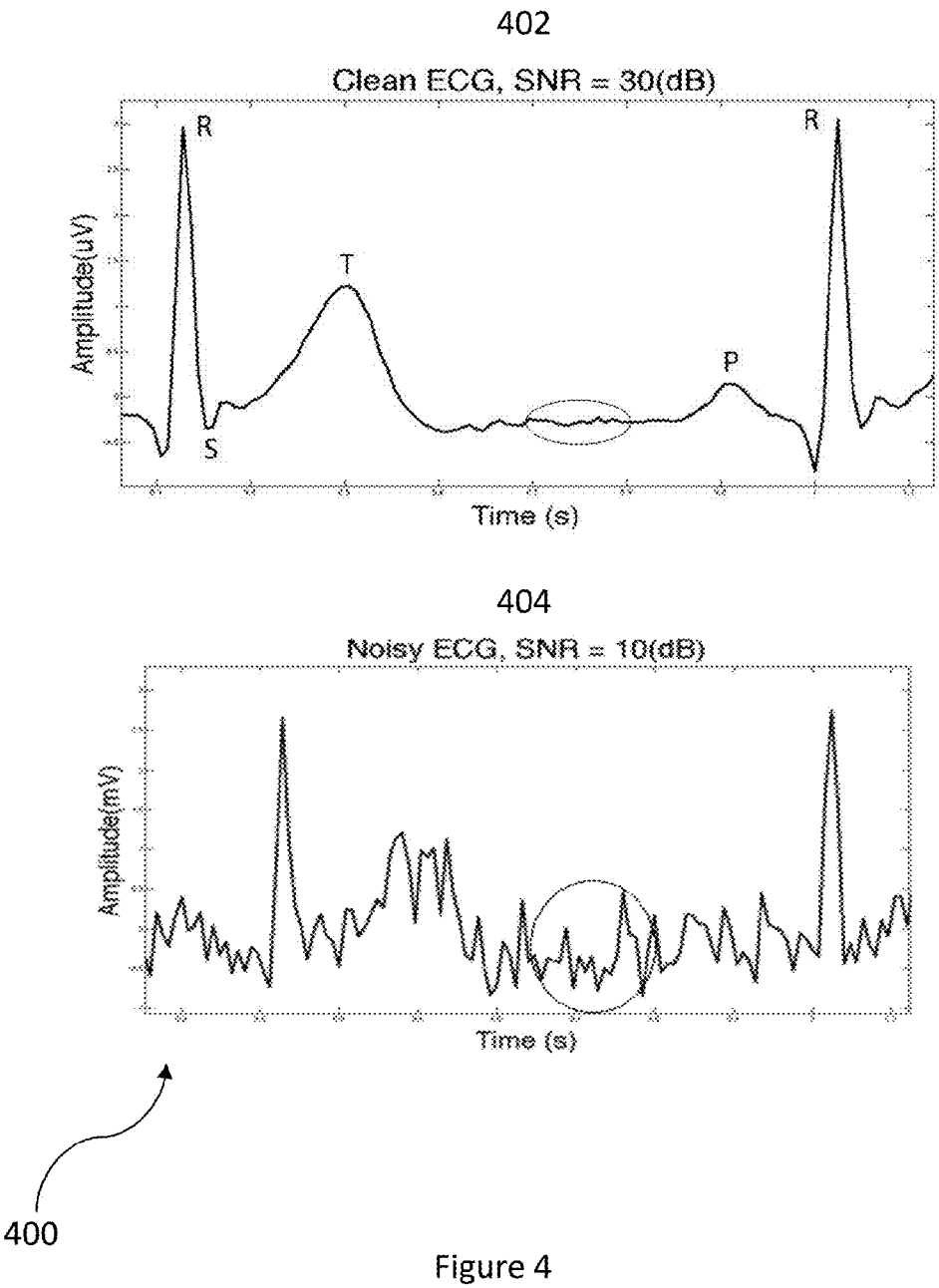
FIG. 4 illustrates a diagram of computing mid-beat SNR in accordance with an embodiment.

FIG. 4 illustrates a diagram 400 of computing mid-beat SNR in accordance with an embodiment. In the diagram 400, the top FIG. 402 shows a clean ECG signal that includes a flat baseline TP segment and the bottom FIG. 404 shows a noisy ECG signal that does not include a flat baseline TP segment and instead includes a TP segment that has many fluctuations.

Figure 5:
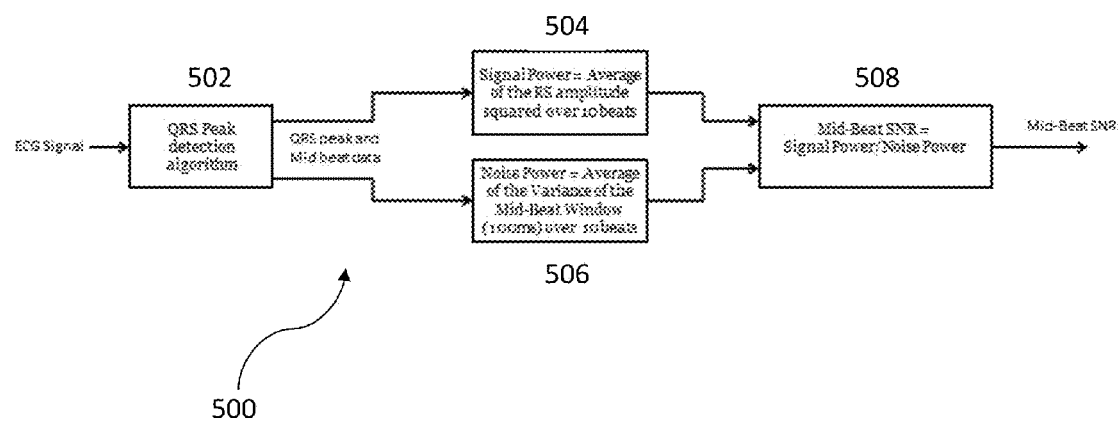
FIG. 5 illustrates a flowchart of computer mid-beat SNR in accordance with an embodiment.

FIG. 5 illustrates a flowchart 500 of computing mid-beat SNR in accordance with an embodiment. In the flowchart 500, an ECG signal is detected by a wireless sensor device 100 and processed by a QRS peak detection algorithm unit 502 which calculates QRS peak and mid-beat data including but not limited to RS amplitude. The QRS peak and mid-beat data is used to calculate the Signal Power via unit 504 and the Noise Power via unit 506. The Signal Power is calculated as the average of the RS amplitude squared over a predetermined number of beats. The Noise Power is calculated as the variance of the mid-beat predetermined time period window over a predetermined number of beats. In one embodiment, the mid-beat predetermined time period window is 100 milliseconds and the predetermined number of beats is 10 beats. The mid-beat SNR is calculated as the ratio of Signal Power/Noise Power via unit 508.

Figure 6:
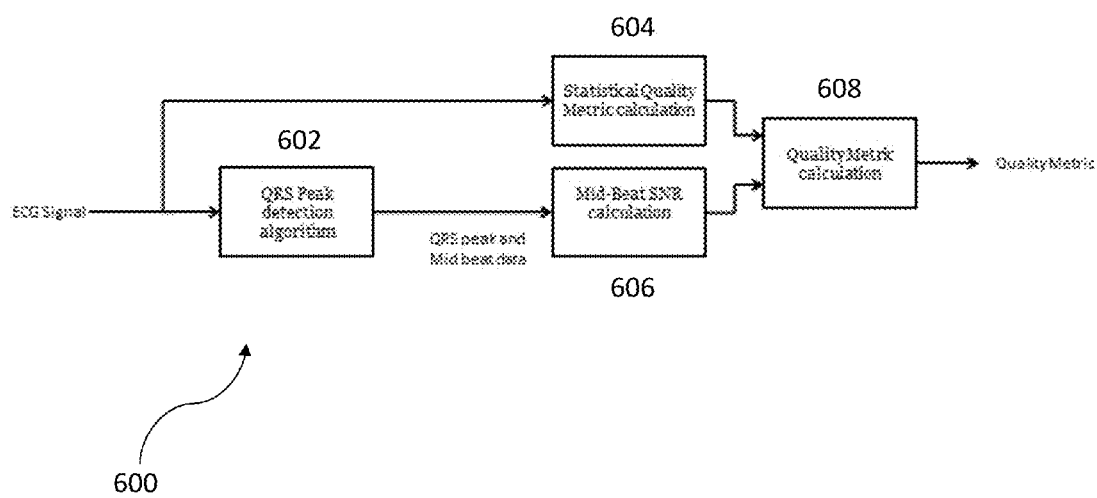
FIG. 6 illustrates a flowchart of a high level overview of the Quality Metric calculation in accordance with an embodiment.

The Quality Metric is calculated by combining the Kurtosis calculation (statistical quality indicator component) and the mid-beat SNR calculation (mid-beat SNR quality indicator component). FIG. 6 illustrates a flowchart 600 of a high level overview of the Quality Metric calculation in accordance with an embodiment. In the flowchart 600, an ECG signal is detected by a wireless sensor device 100 and processed by both a QRS peak detection algorithm unit 602 and a Statistical Quality Metric calculation unit 604. The Statistical Quality Metric calculation unit 604 calculates a Kurtosis of the ECG signal. The QRS peak detection algorithm unit 602 calculates QRS peak and mid-beat data that is used to calculate the mid-beat SNR via the Mid-Beat SNR calculation unit 606. The Quality Metric calculation unit 608 utilizes the outputs of both the Statistical Quality Metric calculation unit 604 and the Mid-Beat SNR calculation unit 606 to calculate the overall Quality Metric of the detected ECG signal.

Figure 7:
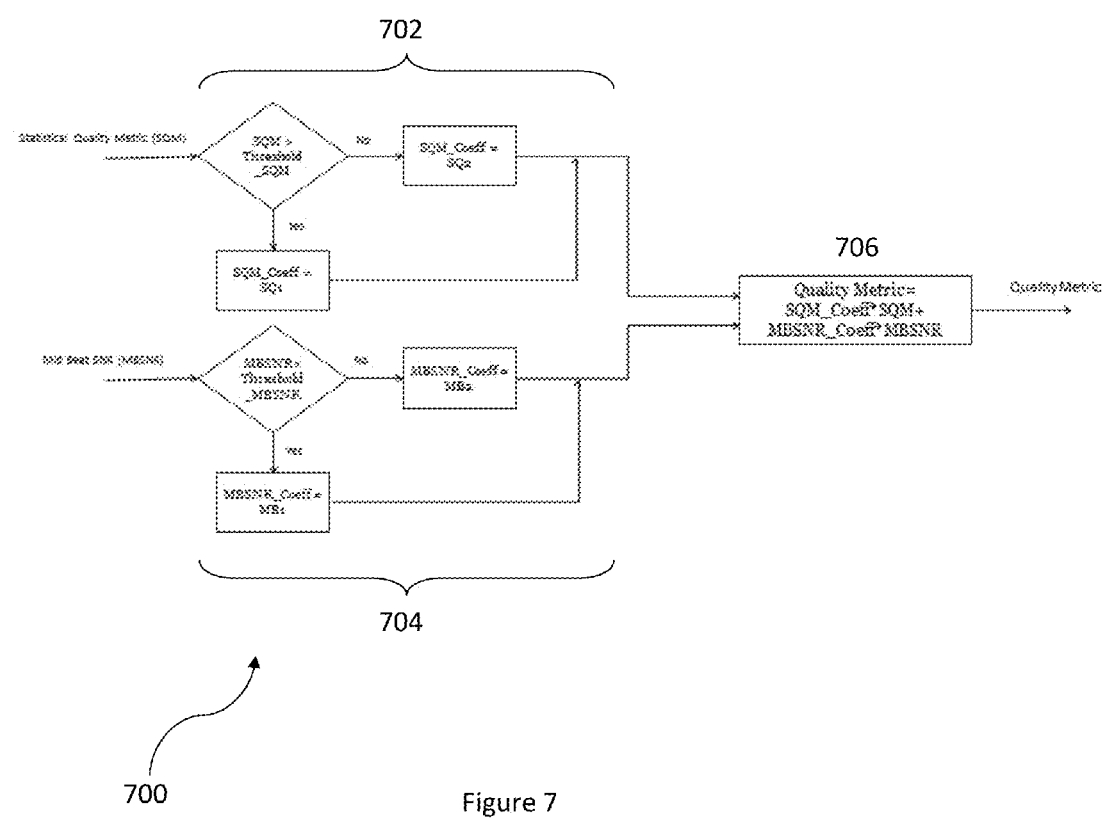
FIG. 7 illustrates a flowchart of a more detailed Quality Metric calculation in accordance with an embodiment.

FIG. 7 illustrates a flowchart 7000 of a more detailed Quality Metric calculation in accordance with an embodiment. Referring to FIGS. 6 and 7 together, after the Kurtosis of the ECG signal (SQM) is calculated via the Statistical Quality Metric calculation unit 604, the SQM is compared to a Threshold_SQM via 702. If SQM is greater than the Threshold_SQM, then SQM_Coeff=SQ1, but if SQM is not greater than the Threshold_SQM, then SQM_Coeff=SQ2. After the mid-beat SNR (MBSNR) is calculated via the Mid-Beat SNR calculation unit 606, the MBSNR is compared to a Threshold_MBSNR via 704. If MBSNR is less than the Threshold_MBSNR, then MBSNR_Coeff=MB1, but if MBSNR is not less than the Threshold_MBSNR, then MBSNR_Coeff=MB2. The overall Quality Metric is calculated via unit 706 per the following weighted linear combination equation: Quality Metric=SQM_Coeff*SQM+MBSNR_Coeff*MBSNR.

In FIG. 7, if SQM (which represents the Kurtosis of the ECG signal) is greater than the Threshold_SQM, that typically indicates that the detected ECG signal is of a higher quality. Therefore, the Kurtosis calculation (statistical quality indicator component) is less sensitive to small noise changes and so is weighted less in the overall Quality Metric calculation by setting SQ1<SQ2. The Kurtosis calculation has a region of low sensitivity when the Kurtosis is a higher value (e.g. 20-25).

Additionally, in FIG. 7, if MBSNR (which represents the mid-beat SNR of the ECG signal) is less than the Threshold_MBSNR, that typically indicates that the detected ECG signal is of a lower quality. Therefore, the mid-beat SNR calculation (mid-beat SNR quality indicator component) is less accurate when detecting beats and so is weighted less in the overall Quality Metric calculation by setting MB1<MB2. The mid-beat SNR calculation has a region of low sensitivity when the mid-beat SNR is a lower value (e.g. below 5 dB).

Figure 8:
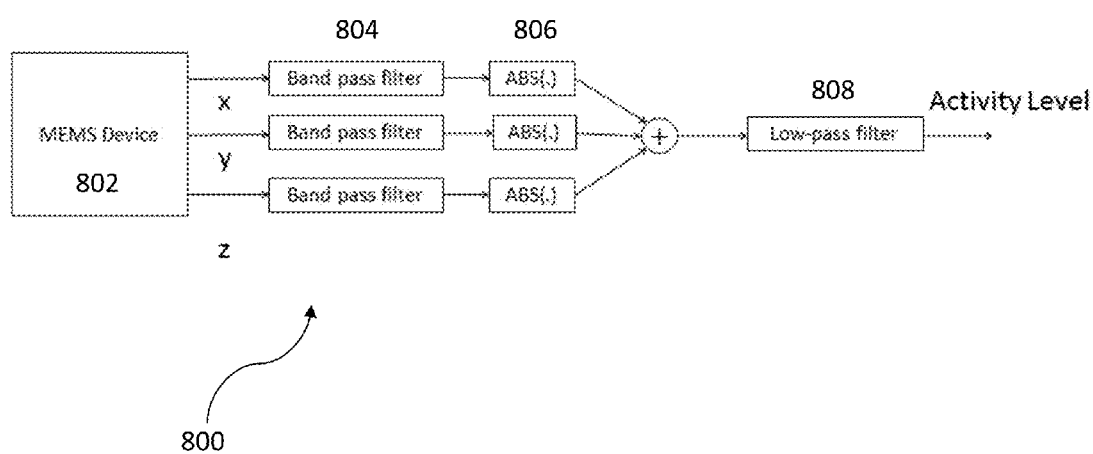
FIG. 8 illustrates a flowchart of computing an activity level in accordance with an embodiment.

FIG. 8 illustrates a flowchart 800 of computing an activity level in accordance with an embodiment. In FIG. 8, the MEMS device 802 detects activity data in x, y, and z coordinates and passes the activity data through three parallel band pass filters 804. An absolute value of the activity data is taken via 806 and the values are summed. The summed values are passed through a low-pass filter 808 which output the activity level. In one embodiment, the parameters of the three parallel band pass filters 804 include but are not limited to a lowpass filter pole of 1 Hz and digital band pass filters with a denominator coefficient vector A=[1024, −992, 32], a numerator coefficient vector B=[496, 0, −496], and a sampling rate fs=62.5 Hz.

Figure 9:
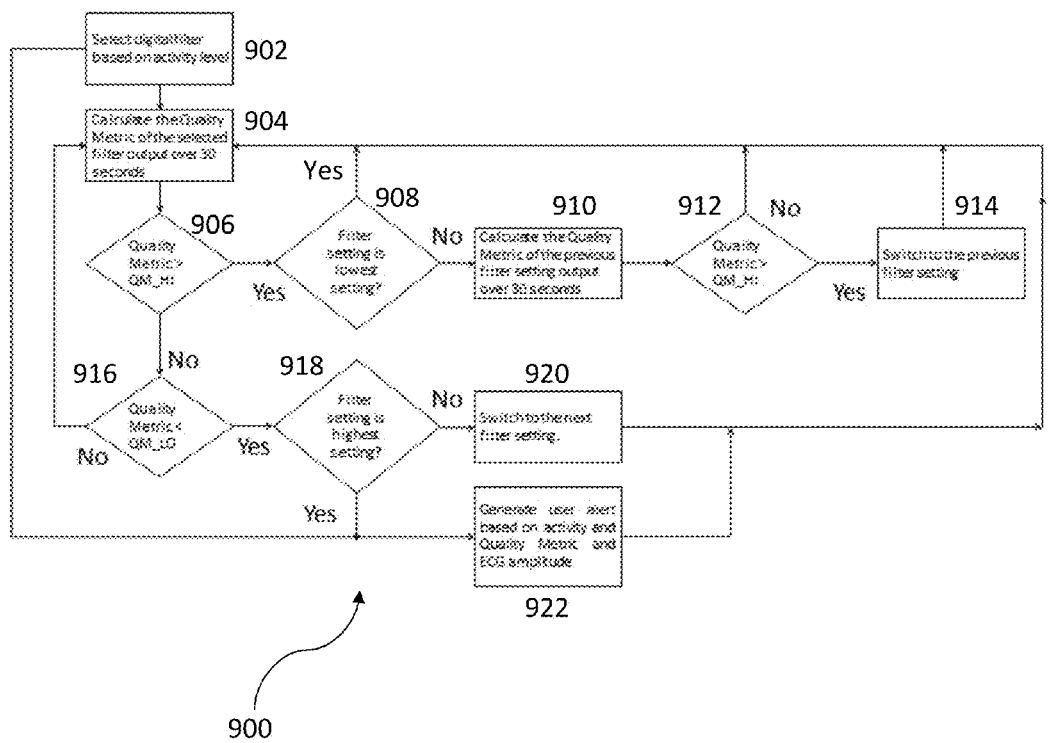
FIG. 9 illustrates a flowchart of adaptive selection of an ECG digital filter in accordance with an embodiment.

FIG. 9 illustrates a flowchart 900 of adaptive selection of an ECG digital filter in accordance with an embodiment. In the flowchart 900, a digital filter is selected based on an activity level that is detected by a MEMS device of the wireless sensor device 100, via step 902. The Quality Metric of the selected digital filter output is calculated over a predetermined time period (e.g. 30 seconds), via step 904. To prevent frequent switching and the lag time that ensues, a minimum ECG Quality Metric is maintained. Maintaining a minimum ECG Quality Metric ensures stability in the selection of the digital filter so that although a higher Quality Metric is available via another digital filter, another digital filter is not selected to prevent erratic switching from occurring.

If the calculated Quality Metric is determined to be greater than QM_HI (which denotes a high quality ECG signal), via step 906, then the flowchart 900 analyzes whether the filter setting is at a lowest cutoff frequency setting of the utilized parallel digital filters, via step 908. If yes (the filter setting is at the lowest cutoff frequency setting), then the ECG signal is at a high quality and optimal processing level and so the flowchart 900 returns back to step 904. If no (the filter setting is not at the lowest cutoff frequency setting), then the Quality Metric of the previous filter setting output is calculated over a predetermined time period (e.g. 30 seconds), via step 910.

The calculated Quality Metric of the previous filter is compared to the threshold QM_HI, via step 912. If the calculated Quality Metric of the previous filter is greater than QM_HI, then the digital filter is switched to the previous filter setting, via step 914, and the flowchart 900 returns back to step 904. If the calculated Quality Metric of the previous filter is not greater than QM_HI, the flowchart 900 returns to step 904.

Referring back to step 906, if the calculated Quality Metric is determined to not be greater than QM_HI, the calculated Quality Metric is compared to QM_LO, via step 916. If the calculated Quality Metric is not less than QM_LO, then it is determined to be between QM_HI and QM_LO and is thus an ECG signal with an average level of quality so there is no need to change the filter and the flowchart 900 returns back to step 904.

If the calculated Quality Metric is less than QM_LO, then the flowchart 900 analyzes whether the filter setting is at a highest cutoff frequency setting of the utilized parallel digital filters, via step 918. If yes (the filter setting is at the highest cutoff frequency setting), then user alters are generated based on activity, Quality Metric, and ECG amplitude stating there are issues with the signal and/or connection. If no (the filter setting is not at the highest cutoff frequency setting), the next filter setting is selected and the flowchart 900 returns back to step 904 to calculate the Quality Metric of the selected next filter setting.

In one embodiment, appropriate notifications are sent to a user of the wireless sensor device 100 in accordance with activity level, Quality Metric, and ECG amplitude calculations. FIG. 10 illustrates a table 1000 of user notifications in accordance with an embodiment. In FIG. 10, if the Quality Metric, QRS amplitude, and activity level are all at a high level, then the diagnosis is a normal ECG signal and there is no action. If the Quality Metric and QRS amplitude are at a high level, and the activity level is at a low level, then the diagnosis is a normal ECG signal and there is no action.

If the Quality Metric and activity level are at a high level, and the QRS amplitude is at a low level, then the diagnosis is a weak but clean ECG signal and the action is to use a digital gain, which involves multiplication of the digital ECG signal by a factor greater than 1. If the Quality Metric is at a high level, and the QRS amplitude and the activity level are both at a low level, then the diagnosis is a weak but clean ECG signal and the action is to use a digital gain.

If the Quality Metric is at a low level, and the QRS amplitude and the activity level are both at a high level, the diagnosis is a noisy ECG signal due to motion artifact, bad skin contact, or wrong placement of the wireless sensor device 100 and the action is to warn the user or wait for the activity to become low and reassess. If the Quality Metric and the activity level are both at a low level, and the QRS amplitude is at a high level, or if the Quality Metric and the QRS amplitude are at a low level, and the activity level is at a high level, or if the Quality Metric, the QRS amplitude, and the activity level are all at a low level, then the diagnosis is a noisy ECG signal due to bad contact or wrong placement and the action is to warn the user if the issues persist.

Figure 11:
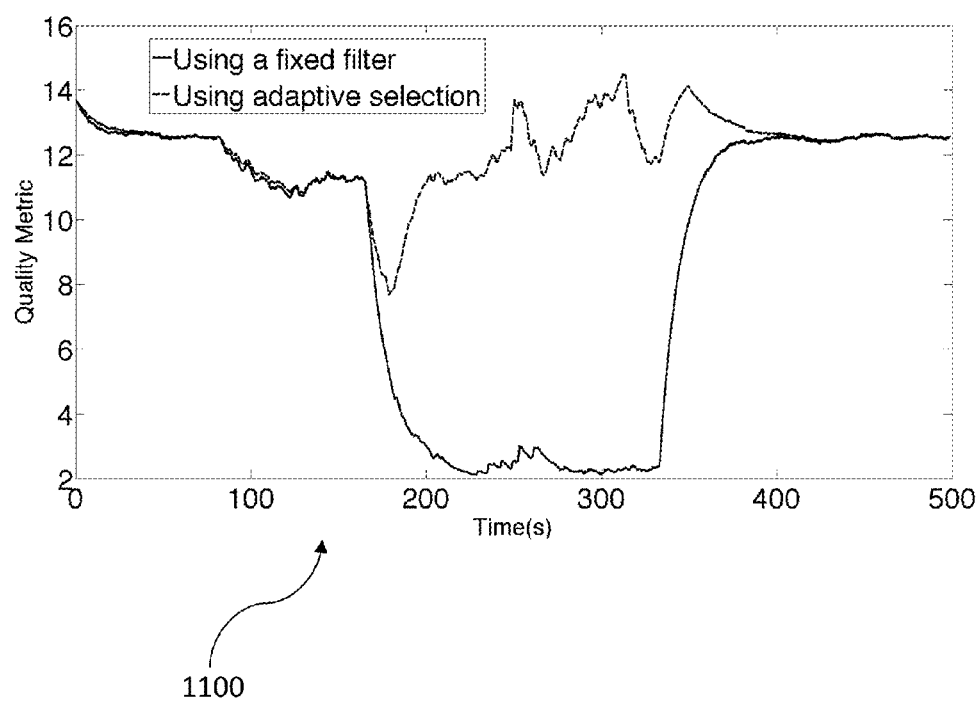
FIG. 11 illustrates a diagram comparing ECG signal quality using a fixed filter and using adaptive selection in accordance with an embodiment.

FIG. 11 illustrates a diagram 1100 comparing ECG signal quality using a fixed filter and using adaptive selection in accordance with an embodiment. In the diagram 1100, the quality metric of the fixed filter approach significantly drops between the 200-300 seconds time period whereas the quality metric of the adaptive selection approach remains relatively stable at a quality metric value above 10 between the 200-300 seconds time period.

Figure 12:
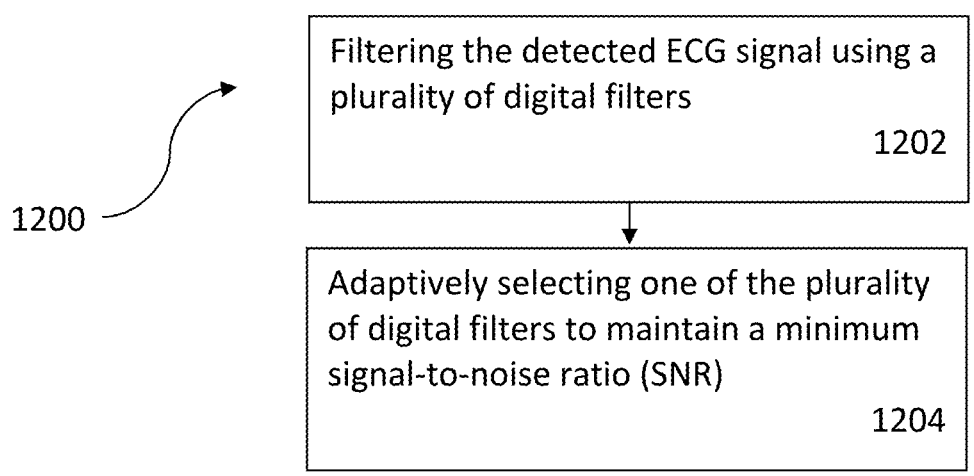
FIG. 12 illustrates a method for filtering a detected ECG signal in accordance with an embodiment.

FIG. 12 illustrates a method 1200 for filtering a detected ECG signal in accordance with an embodiment. The method 1200 includes filtering the detected ECG signal using a plurality of digital filters, via step 1202. The method 1200 includes adaptively selecting one of the plurality of digital filters to maintain a minimum signal-to-noise ratio (SNR), via step 1204. In one embodiment, the plurality of digital filters includes a plurality of parallel digital band-pass filters with varying high-pass cutoff frequencies (e.g. 1-20 Hz).

In one embodiment, the method 1200 further includes utilizing an output of the adaptively selected digital filter to calculate features of the detected ECG signal including but not limited to RR intervals. The method 1200 further includes calculating a Quality Metric for each of the plurality of digital filters, wherein the Quality Metric is utilized to adaptively select one of the plurality of digital filters. In one embodiment, the calculating is carried out on only one of the plurality of digital filters at a time to conserve power consumption related to the processing required for the calculating.

In one embodiment, the calculating of the Quality Metric comprises calculating a statistical quality indicator (e.g. a Kurtosis calculation of the detected ECG signal) and calculating a mid-beat SNR quality indicator (e.g. the ratio of the Signal Power/Noise Power) and then combining these two quality indicators via a weighted linear combination. The method 1200 further includes calculating an activity level using a microelectromechanical systems (MEMS) device that is embedded within the wireless sensor device 100 to measure noise of the detected ECG signal.

In one embodiment, the method 1200 further includes maintaining a minimum Quality Metric to prevent erratic switching between the plurality of digital filters by comparing various high and low level thresholds to the calculated Quality Metrics for each output of the plurality of digital filters. In one embodiment, the method 1200 further includes providing notifications of ECG signal quality and recommended actions for a user or operator of the wireless sensor device 100. The notifications are based upon the calculated Quality Metric, the calculated activity level, and various other factors including but not limited to QRS amplitude.

As above described, the method and system allow for filtering a detected ECG signal using adaptive selection of digital filters to maintain a minimum signal-to-noise ratio (SNR) and ECG signal quality. A wireless sensor device detects an ECG signal which is then filtered using a plurality of dynamically adjusting digital filters. A Quality Metric is calculated for each of the plurality of digital filters using both a statistical component and a mid-beat SNR component. The Quality Metric is used in combination with a detected activity level to adaptively select one of the plurality of digital filters that maintains a minimum ECG quality level thereby arriving at more accurate ECG signal based calculations.

A method and system for filtering a detected ECG signal has been disclosed. Embodiments described herein can take the form of an entirely hardware implementation, an entirely software implementation, or an implementation containing both hardware and software elements. Embodiments may be implemented in software, which includes, but is not limited to, application software, firmware, resident software, microcode, etc.

The steps described herein may be implemented using any suitable controller or processor, and software application, which may be stored on any suitable storage location or computer-readable medium. The software application provides instructions that enable the processor to cause the receiver to perform the functions described herein.

Furthermore, embodiments may take the form of a computer program product accessible from a computer-usable or computer-readable storage medium providing program code or program instructions for use by or in connection with a computer or any instruction execution system. For the purposes of this description, a computer-usable or computer-readable storage medium can be any apparatus that can contain, store, communicate, propagate, or transport the program for use by or in connection with the instruction execution system, apparatus, or device.

The computer-readable storage medium may be an electronic, magnetic, optical, electromagnetic, infrared, semiconductor system (or apparatus or device), or a propagation medium. Examples of a computer-readable storage medium include a semiconductor or solid state memory, magnetic tape, a removable computer diskette, a random access memory (RAM), a read-only memory (ROM), a rigid magnetic disk, and an optical disk. Current examples of optical disks include DVD, compact disk-read-only memory (CD-ROM), and compact disk-read/write (CD-R/W).

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for filtering a detected ECG signal using a plurality of digital filters, the method comprising:
   calculating a kurtosis of a detected ECG signal as a statistical quality indicator;
   calculating a mid-beat signal-to-noise ratio (SNR) by analyzing successive QRS peaks of the detected ECG signal;
   calculating a quality metric for a plurality of digital filters by combining the statistical quality indicator and the mid-beat signal-to-noise ratio (SNR),
      wherein the statistical quality indicator and the mid-beat SNR quality indicator are combined via a weighted linear combination; and
   adaptively selecting one of the plurality of digital filters by comparing the calculated quality metric to a minimum quality metric threshold and by determining a cutoff frequency setting of the one of the plurality of digital filters to prevent erratic switching between the plurality of digital filters.

2. The method of claim 1, wherein the plurality of digital filters comprise a plurality of parallel digital band-pass filters with varying high-pass cutoff frequencies.

3. The method of claim 1, further comprising:
   utilizing an output of the adaptively selected digital filter to calculate an RR interval of the detected ECG signal.

4. The method of claim 1, wherein the calculating the quality metric is only on one of the plurality of digital filters at a time to conserve power consumption.

5. The method of claim 1, further comprising:
   calculating an activity level using a microelectromechanical systems (MEMS) device embedded within a wireless sensor device to measure noise of the detected ECG signal.

6. The method of claim 5, further comprising:
   providing notifications of ECG signal quality and recommended actions based upon the calculated Quality Metric and the calculated activity level.

7. The method of claim 1, wherein the calculating of the mid-beat SNR further comprises:
   calculating a ratio of signal power over noise power.

8. The method of claim 7, wherein the noise power is calculated as a variance of the detected ECG signal over a predetermined time period in a middle of a TP segment that is averaged over a plurality of beats.

9. The method of claim 8, wherein the signal power is calculated as an average of RS amplitude squared over the plurality of beats.

10. The method of claim 1, wherein the statistical quality indicator is weighted less during the calculation of the quality metric when the detected ECG signal is of a higher quality.

11. The method of claim 1, wherein the mid-beat SNR is weighted less during the calculation of the quality metric when the detected ECG signal is of a lower quality.

* * * * *